(12) United States Patent
Fujita et al.

(10) Patent No.: US 6,717,677 B2
(45) Date of Patent: Apr. 6, 2004

(54) FILM DEFECT INSPECTION METHOD FOR A FILM FORMED ON A SUBSTRATE

(75) Inventors: Sayaka Fujita, Kashihara (JP); Yoichi Takesawa, Toyonaka (JP); Yoshihide Shimoda, Nara (JP); Tatsuhiro Morita, Kashiba (JP); Rikiya Matsuo, Nara (JP); Masayuki Sakamoto, Nabari (JP); Koichi Toriyama, Yamatokoriyama (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 10/244,679

(22) Filed: Sep. 17, 2002

(65) Prior Publication Data

US 2003/0035110 A1 Feb. 20, 2003

Related U.S. Application Data

(63) Continuation of application No. 09/545,595, filed on Apr. 7, 2000.

(30) Foreign Application Priority Data

Apr. 9, 1999 (JP) .......................................... P11-102915
Nov. 10, 1999 (JP) .......................................... P11-320195

(51) Int. Cl.[7] ................................................ G01B 9/02
(52) U.S. Cl. ...................................... 356/450; 356/504
(58) Field of Search ............................... 356/450, 511, 356/512, 497, 446, 504; 355/35

(56) References Cited

U.S. PATENT DOCUMENTS 4,548,506 A 10/1985 Elson
4,904,557 A 2/1990 Kubo

FOREIGN PATENT DOCUMENTS

| EP | 0 358 936 A2 | 3/1990 |
| JP | 4-336540 A | 11/1992 |
| JP | 6-130683 A | 5/1994 |

OTHER PUBLICATIONS

Sinha et al, Infrared interferometry for rough surface measurements: application to failure characterizations and flaw detection, SPIE Optical Engineering, pp. 2233–2239, Aug. 1997.*

* cited by examiner

Primary Examiner—Samuel A. Turner
(74) Attorney, Agent, or Firm—Nixon & Vanderhye PC

(57) ABSTRACT

It is an object of the invention to inspect defects of a film formed on a relatively rough surface of a substrate by the light interference method. A substrate on which a film is formed is irradiated with light of a longer wavelength than the surface roughness Rmax or Rz of the substrate to obtain interference fringes to inspect defects of the film formed on the substrate. Especially, it is preferable that when the surface roughness Rmax or Rz is 0.5 μm or more, the substrate is irradiated with light of a wavelength beyond a little longer wavelength than the surface roughness Rmax or Rz. The surface of the substrate is subjected to a cutting process. Specifically, it is possible to inspect defects of the electric charge generation layer, electric charge transport layer, or undercoat layer of an electrophotographic photoreceptor. This photoreceptor is mounted in a digital copier or printer. Further, monochromatic light is preferably applied. Alternatively, indirect light of the light reflected from a reflector plate or the light diffused by a diffusing plate is preferably applied.

18 Claims, 12 Drawing Sheets

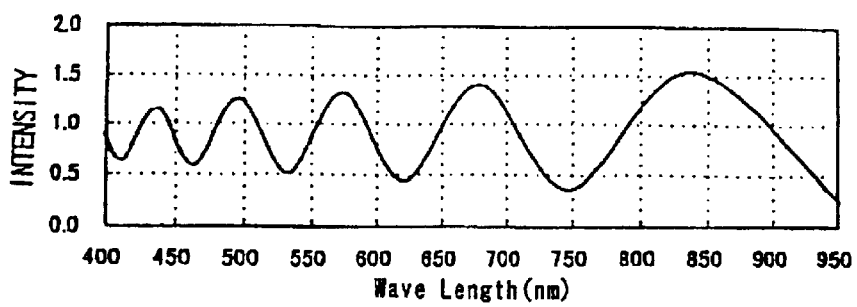
FIG. 4A  INTERFERENCE PATTERN DUE TO h1b
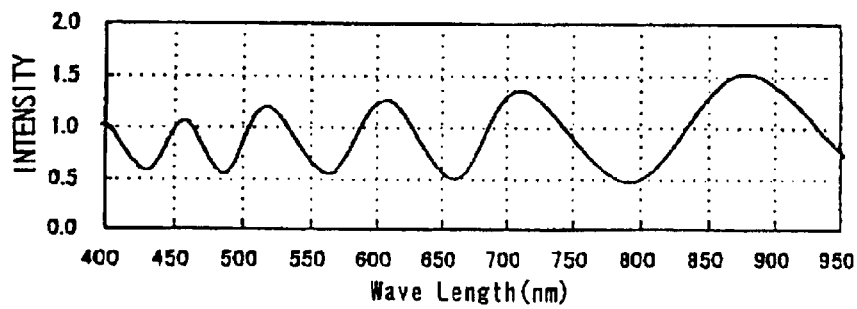
FIG. 4B  INTERFERENCE PATTERN DUE TO h2b
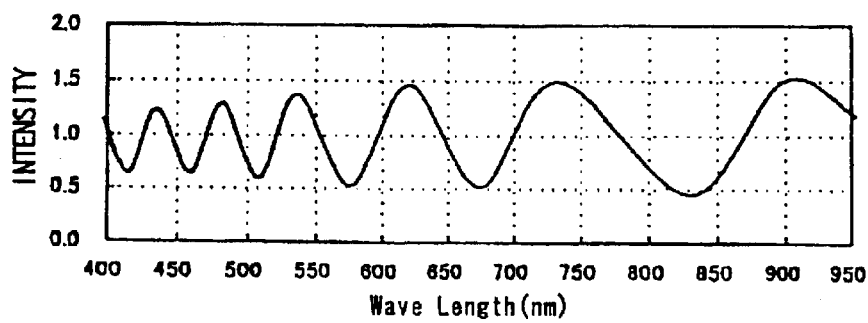
FIG. 4C  INTERFERENCE PATTERN DUE TO h3b
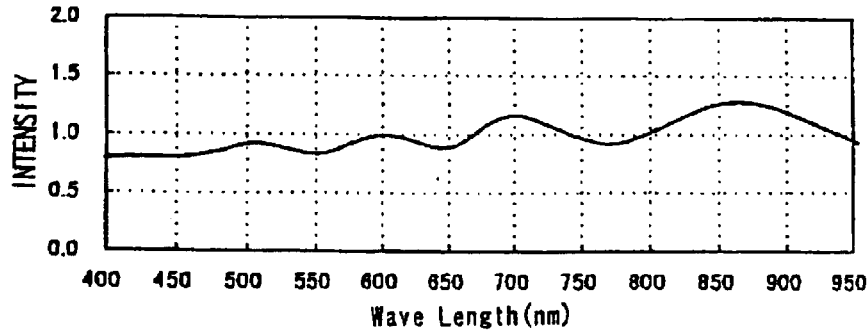
FIG. 4D  SYNTHETIC WAVE OF THE INTERFERENCE PATTERNS DUE TO h1b TO h3b

FIG. 8A

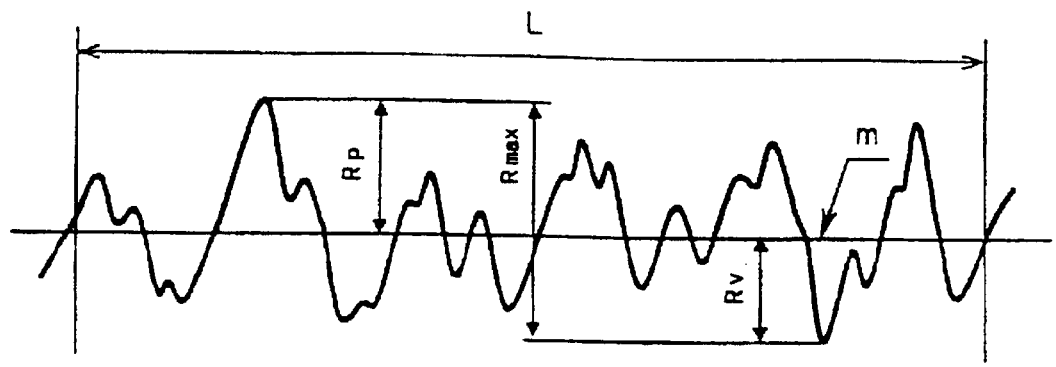

- Rmax : MAXIMUM HEIGHT
- m : MEAN LINE
- L : STANDARD LENGTH

FIG. 8B

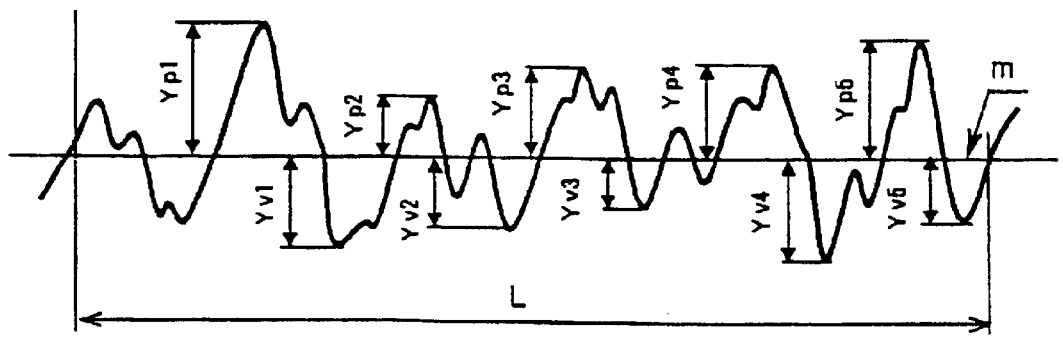

$Rz = (|Yp1+Yp2+Yp3+Yp4+Yp5| + |Yv1+Yv2+Yv3+Yv4+Yv5|)/5$

- $Yp1, Yp2, Yp3, Yp4, Yp5$ : ALTITUDE FROM HIGHEST PEAK TO FIFTH PEAK OF EXTRACTED PORTION CORRESPONDING TO STANDARD LENGTH L
- $Yv1, Yv2, Yv3, Yv4, Yv5$ : ALTITUDE FROM LOWEST VALLEY TO FIFTH VALLEY OF EXTRACTED PORTION CORRESPONDING TO STANDARD LENGTH L
- Rz : 10-POINT AVERAGE ROUGHNESS
- m : MEAN LINE
- L : STANDARD LENGTH

US 6,717,677 B2

FILM DEFECT INSPECTION METHOD FOR A FILM FORMED ON A SUBSTRATE

This application is a continuation of application Ser. No. 09/545,595, filed Apr. 7, 2000, the entire content of which is hereby incorporated by reference in this application.

BACKGROUND OF THE INVENTION

1. Field of the Invention

The present invention relates to a film defect inspection method for a film formed on a substrate, such as an electric charge generation layer, electric charge transport layer or undercoat layer formed on a relatively rough surface of a conductive substrate of an electrophotographic photoreceptor to be mounted in a digital copier or printer.

2. Description of the Related Art

A method for manufacturing an electrophotographic photoreceptor (hereinafter, also simply referred to as "photoreceptor") with a uniform film thickness and electric characteristics is disclosed in Japanese Unexamined Patent Publications JP-A 4-336540 (1992) and 6-130683 (1994). In this method the film thickness of an undercoat layer or electric charge transport layer formed on a conductive substrate (hereinafter referred to as "substrate") of the photoreceptor is controlled and the amount of applied paint is adjusted.

Paints for the electric charge generation layer, electric charge transport layer, and undercoat layer are applied onto the substrate by a dip coating method which is particularly excellent in productivity among various methods. The dip coating method is accomplished by dipping the substrate in a tank filled with the paint, and subsequently raising the substrate therefrom at a constant speed. However, the organic solvent in the paint tends to evaporate, and variations in coating thickness tend to occur due to a change in viscosity of the paint.

The film thickness of each functional film of the photoreceptor is an important factor for determining the sensitivity, and should be severely controlled. Although examples of the film thickness measuring method include the contact type, non-contact type, and photograph type, the non-contact type whereby the coating itself will not be marred is preferable. The light interference method is particularly preferable because it is capable of measuring the film thickness of the layer containing no pigment such as the electric charge transport layer or undercoat layer. It is also excellent in accuracy of measurement and resolving power, and requires no particular facilities. In JP-A 4-336540 and JP-A 6-130683, the film thickness is successively measured by the light interference method, and the results of the measurement are fed back to automatically control the coating speed to an appropriate speed.

The variations in film thickness of each functional film of the photoreceptor also cause surface potential variations. The surface potential variations make it impossible to obtain a uniform half-tone image. Further, inclusion of foreign matters results in black points and white points occurring on the image. Therefore, defects such as variations in film thickness and inclusion of foreign matters need to be severely inspected.

The inspection of defects such as variations in film thickness or inclusion of foreign matters is also accomplished by the light interference method. Specifically, it is accomplished by the visual evaluation of the interference fringes occurring on the film surface when the film on the substrate is irradiated with light. In the case where irregularities or discontinuous portions occur in the interference fringes, it is judged that defects of some kind such as variations in film thickness and inclusion of foreign matters occur.

Such a film thickness measurement and defect inspection by the light interference method are possible for the lamination-type photoreceptor having a transparent film because interference of irradiation light occurs therein. However, it is impossible for the monolayer-type photoreceptor wherein electric charge generation substances such as pigment are dispersed in the film because the irradiation light is absorbed or scattered by the electric charge generation substances and hence undergoes no interference.

The light interference method cannot be directly applied to the film formed on the substrate whose surface is made relatively rough in order to control the light interference. In recent years, digital electrophotographic photoreceptor mounted in digital color copiers or printers have replaced analog electrophotographic photoreceptors. In the digital photoreceptor, the conductive substrate surface is subjected to a surface-roughening treatment in order to inhibit the interference fringes resulting from the light reflected from the substrate surface and the light reflected from the film surface. Thus, in the substrate whose surface is relatively rough, the rays of light from the substrate surface and the film surface are less likely to interfere with each other, and the rays of light are scattered. Accordingly, film thickness measurement and defect inspection by the light interference method are difficult.

Further, the clearer the interference fringes are, the more the accuracy of the defect inspection is improved. However, in the digital electrophotographic photoreceptor, the interference of light is less likely to occur due to the foregoing surface-roughening treatment, and hence the interference fringes become obscure. Accordingly, the inspection accuracy is reduced. Consequently, the load on the inspector increases, and thus the inspection time becomes longer, resulting in a reduction in productivity.

SUMMARY OF THE INVENTION

It is an object of the invention to provide a film defect inspection method for inspecting defects such as film thickness variations and inclusion of foreign matters of a film formed on a substrate whose surface is relatively rough, by the light interference method.

The invention provides a film defect inspection method for inspecting defects of a film formed on a substrate by a light interference method, comprising:

irradiating the substrate with light of a longer wavelength than a surface roughness Rmax of the substrate.

According to the invention, the substrate on which a film is formed is irradiated with light of a longer wavelength than the surface roughness Rmax of the substrate. By thus optimizing the wavelength of the irradiation light, the interference fringes can be obtained, and thus the film defects can be inspected.

Further, in the film defect inspection method of the invention, it is preferable that the substrate is irradiated with light of a wavelength of 500 nm or more when the surface roughness Rmax of the substrate is 0.5 µm or more.

According to the invention, it is preferable that the substrate is irradiated with light of a wavelength of 500 nm or more especially when the surface roughness Rmax of the substrate is 0.5 µm or more. Consequently, the interference fringes can be obtained with reliability, and the inspection of the film defects becomes possible.

Further, in the film defect inspection method of the invention, it is preferable that when the surface roughness Rmax of the substrate is 0.5 μm or more, the substrate is irradiated with light of a wavelength beyond a little longer wavelength than the surface roughness Rmax.

According to the invention, in particular, when the surface roughness Rmax of the substrate is 0.5 μm or more, the substrate is irradiated with light of a wavelength beyond a little longer wavelength than the surface roughness Rmax. Consequently, the interference fringes can be obtained with reliability, and the inspection of the film defects becomes possible.

Further, the invention provides a film defect inspection method for inspecting defects of a film formed on a substrate by a light interference method, comprising:

irradiating the substrate with light of a longer wavelength than a surface roughness Rz of the substrate.

According to the invention, the substrate on which a film is formed is irradiated with light of a longer wavelength than the surface roughness Rz of the substrate. By thus optimizing the wavelength of the irradiation light, interference fringes can be obtained, and the film defects can be inspected.

Further, in the film defect inspection method of the invention it is preferable that when the surface roughness Rz of the substrate is 0.5 μm or more, the substrate is irradiated with light of a wavelength of 500 nm or more.

According to the invention, in particular, when the surface roughness Rz of the substrate is 0.5 μm or more, the substrate is irradiated with light of a wavelength of 500 nm or more. Consequently, interference fringes can be obtained with reliability, and the inspection of film defects becomes possible.

Further, in the film defect inspection method of the invention it is preferable that when the surface roughness Rz of the substrate is 0.5 μm or more, the substrate is irradiated with light of a wavelength beyond a little longer wavelength than the surface roughness Rz.

According to the invention, especially when the surface roughness Rz of the substrate is 0.5 μm or more, the substrate is irradiated with light of a wavelength beyond a little longer wavelength than the surface roughness Rz. Consequently, the interference fringes can be obtained with reliability, and the inspection of film defects becomes possible.

Further, in the film defect inspection method of the invention, it is preferable that the substrate surface is subjected to a cutting work.

According to the invention, a film is formed on the substrate whose surface is relatively rough due to the cutting work. Such a substrate is irradiated with the foregoing optimized light. The interference fringes can also be obtained in this case, and the inspection of film defects becomes possible.

In the film defect inspection method of the invention, it is preferable that the substrate is electrically conductive, and on the substrate are formed an electric charge generation layer, and an electric charge transport layer or an undercoat layer, which constitute an electrophotographic photoreceptor along with the substrate.

According to the invention, specifically, the defects of the electric charge generation layer and electric charge transport layer or undercoat layer of the electrophotographic photoreceptor can be inspected.

Further, in the film defect inspection method of the invention, it is preferable that the electrophotographic photoreceptor is one for digital copiers or printers According to the invention, it is possible to inspect the defects of the foregoing layers of the electrophotographic photoreceptor in which the layers are provided on the substrate having a relatively rough surface, that is, the electrophotographic photoreceptor to be mounted in a digital copier or printer.

Further, in the film defect inspection method of the invention, it is preferable that the substrate is irradiated with monochromatic light or indirect light, and the indirect light is light reflected from a reflector plate or light diffused by a diffusing plate.

According to the invention, by irradiation with monochromatic light, clearer interference fringes can be obtained. Therefore, the film defect inspection with high accuracy becomes possible. Further, by irradiation with indirect light, the interference fringes can be obtained over the wide range, and hence a reduction in inspection time can be achieved. Thus, film defects can be inspected with efficiency to improve productivity.

Further, in the film defect inspection method of the invention, it is preferable that the film defect inspection is an inspection of variations in film thickness or an inspection of foreign matters in the film.

According to the invention, it is possible to inspect the defects of variations in film thickness and inclusion of foreign matters by interference fringes.

BRIEF DESCRIPTION OF THE DRAWINGS

Other and further objects, features, and advantages of the invention will be more explicit from the following detailed description taken with reference to the drawings wherein.

FIGS. 4A to 4C are graphs showing their respective interference spectra by reflected light rays h1b to h3b, and FIG. 4D is a graph showing the combined spectrum of the interference spectra by the reflected light rays h1b to h3b;

FIGS. 8A and 8B are diagrams for illustrating the surface roughnesses Rmax, Rz, respectively;

DETAILED DESCRIPTION OF THE PREFERRED EMBODIMENTS

Figure 1A:
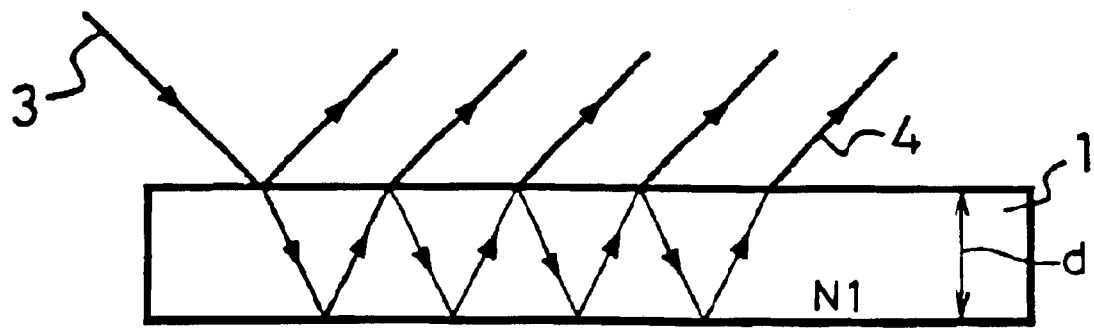
FIGS. 1A and 1B are views for explaining the principle of a film defect inspection method by the light interference method of the invention.

Now referring to the drawings, preferred embodiments of the invention are described below.

Figure 1B:
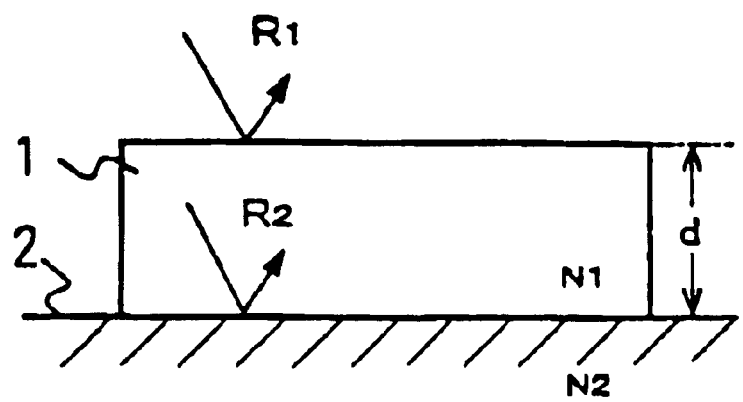

First, the principle of a film defect inspection method by the light interference method will be explained. The principle of the film defect inspection method by the light interference method is the same as the principle of the film thickness measuring method. FIGS. 1A and 1B are views for explaining the principle. When light 3 is incident upon a transparent film 1 with a film thickness d and a refractive index N1, multiple reflection of the light occurs inside the film 1 as shown in FIG. 1A. The reflected light 4 is the one obtained by synthesizing the light rays which have passed through the inside of the film 1 plural times. The rays of reflected light 4 intensify each other in the case where a difference between adjacent phases is an integral multiple of $2\pi$, while they cancel each other in the case of an odd multiple of $\pi$, by the interference of light.

The reflectance R when light is incident upon the film 1 formed on the substrate 2 as shown in FIG. 1B is represented by the formula (1):

$$R = [R1^2 + R2^2 - 2R1R2 \cos(X)] / [1 + R1^2 + R2^2 - 2R1R2 \cos(X)] \quad (1)$$

wherein $R1 = (1-N1)/(1+N1)$
$R2 = (N1-N2)/(N1+N2)$
$X = 4\pi N1 d/\lambda$
$N2 > N1$;

$\lambda$: wavelength, d: thickness of the film 1, R1: reflectance on the surface of the film 1, R2: reflectance on the surface of the substrate 2, N1: refractive index of the film 1, and N2: refractive index of the substrate 2.

The reflectance takes a maximum value at wavelengths intesifying each other, while it takes a minimum value at wavelengths canceling each other, by the interference of light. The reflectance R is differentiated with the wavelength $\lambda$, and the peak wavelength $\lambda n$ leading to $(d/d\lambda)R(\lambda) = 0$ is determined, thereby yielding an equation (2):

$$(1/\lambda n) - (1/\lambda n+1) = 1/2N1d \quad (2)$$

wherein $\lambda n$: the wavelength having the nth maximum value or minimum value.

In the case where the peak wavelengths $\lambda n$ intensifying or canceling each other, and the refractive index N1 of the film 1 are found by the equation (2), the thickness d of the film 1 can be determined. The peak wavelengths $\lambda n$ intensifying or canceling each other, and the refractive index N1 of the film 1 can be measured with a spectrophotometer. Therefore, the thickness d of the film 1 can be determined. It is noted that, in the case where the refractive index N1 of the film 1 is unknown, it can be determined from the equation (2) by the light interference method using a standard sample having a known film thickness.

Here, the peak wavelength $\lambda n$ due to the interference of light is represented by equation (3). The equation (3) indicates that the distance between the peak wavelengths $\lambda n$ decreases with a decrease in wavelength.

$$\lambda n = 4dN1/(2n-1) \quad (3)$$

Figure 2:
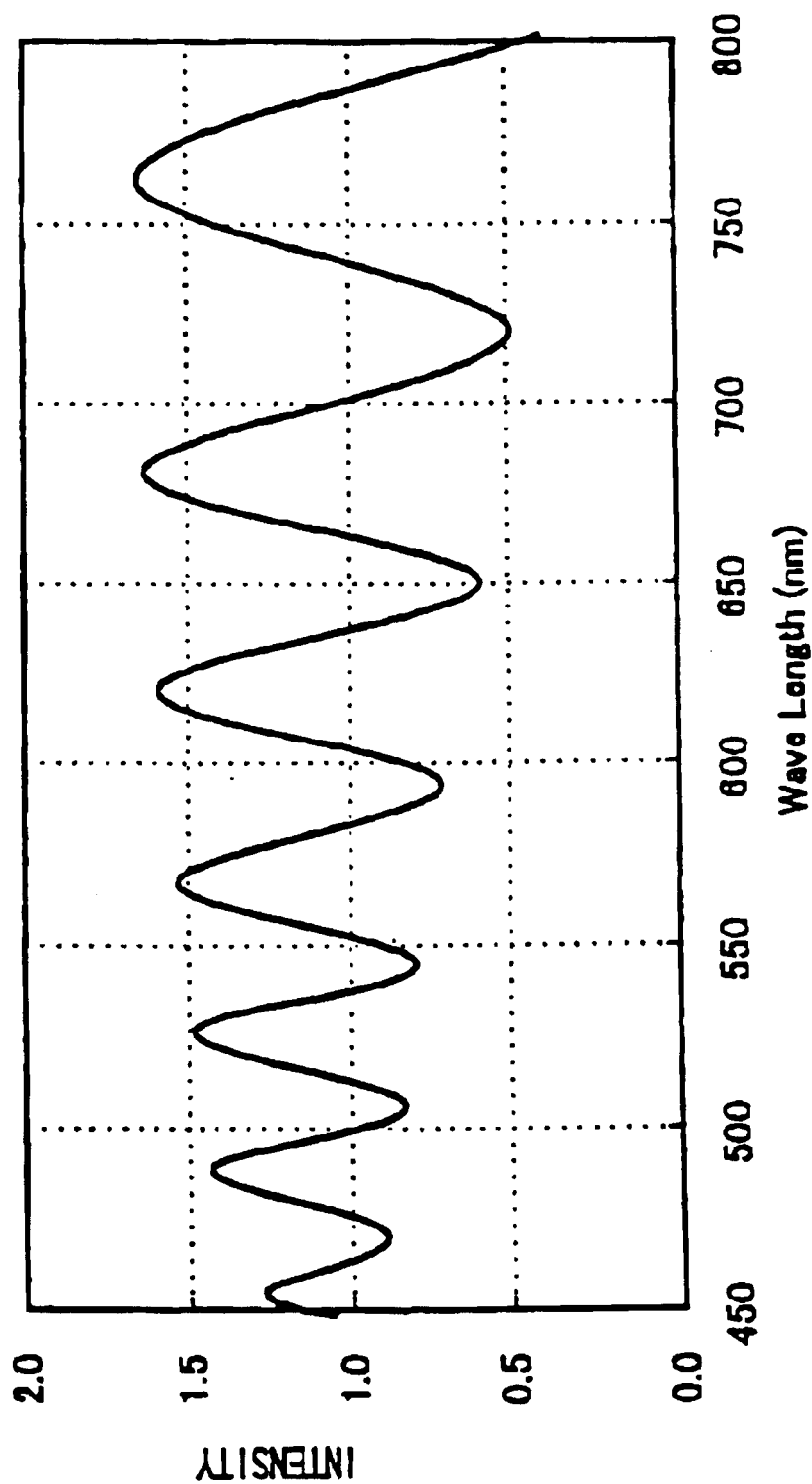
FIG. 2 is a graph showing a peak wavelengths λn of a film 1 formed on a mirror-finished substrate 2.

FIG. 2 is a graph showing the peak wavelengths $\lambda n$ of the film 1 with a refractive index N1 of 2.0 formed on the mirror-finished substrate 2 made of aluminium. The peak wavelengths $\lambda n$ arising from the interference are 455, 488, 525, 568, 620, 683, and 762 nm. Substitution of these peak wavelengths $\lambda n$ into the equation (2) yields each film thickness d of the film 1 for every peak wavelength. Table 1 shows each film thickness d determined.

TABLE 1

| $\lambda p$ (nm) | Calculated film thickness ($\mu$m) |
|---|---|
| 455 | — |
| 488 | 1.620* |
| 525 | 1.731 |
| 568 | 1.734 |
| 620 | 1.693 |
| 683 | 1.680 |
| 762 | 1.647 |
| | Mean value 1.684 |

*Film thickness obtained by substituting two values as $\lambda n = 455$, $\lambda n + 1 = 488$, into the equation (2).

Each film thickness hereinafter was calculated in the same manner.

The film thicknesses d corresponding to their respective peak wavelengths $\lambda n$ sequentially from the shorter wavelength side are 1.620, 1.731, 1.734, 1.693, 1.680, and 1.647 $\mu$m. However, the film thicknesses d are originally equal to one another, and hence these values are subjected to an arithmetic mean processing. Consequently, a film thickness d=1.684 $\mu$m can be obtained.

It is noted that, the more the number of data to be subjected to the arithmetic mean processing, the more preferable, in order to obtain a film thickness d with high reliability. In order to increase the number of data, it is preferable to use light of a short wavelength which will give a large number of the peak wavelengths $\lambda n$ arising from the interference of light within a constant wavelength range.

Figure 3A:
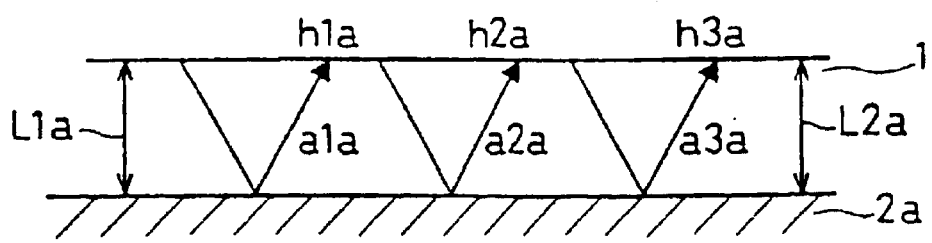
FIG. 3A is a view showing reflection optical path lengths a1a–a3a of rays of light incident upon the film 1 formed on a substrate 2a whose surface is relatively smooth.
Figure 3B:
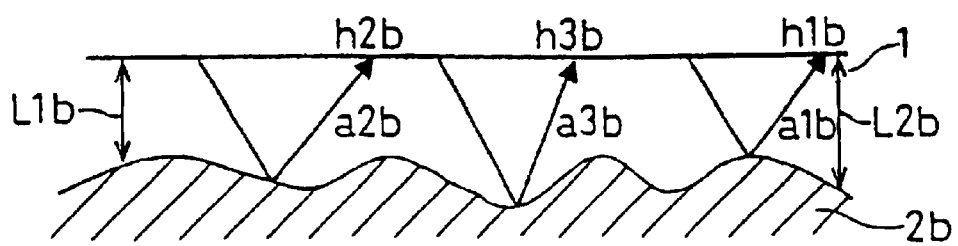
FIG. 3B is a view showing reflection optical path lengths a1b–a3b of rays of light incident upon the film 1 formed on a substrate 2b whose surface is relatively rough.

FIG. 3A is a view showing reflection optical path lengths a1a–a3a of rays of light incident upon the film 1 formed on a substrate 2a whose surface is relatively smooth, and FIG. 3B is a view showing reflection optical path lengths a1b–a3b of rays of light incident upon the film 1 formed on a substrate 2b whose surface is relatively rough. FIGS. 4A to 4C are graphs showing their respective interference spectra by reflected light rays h1b to h3b, and FIG. 4D is a graph showing the combined spectrum of the interference spectra by the reflected light rays h1b to h3b.

In the electrophotographic photoreceptor for analog use, the film 1 is formed on the substrate 2a whose surface is smooth. In the photoreceptor, the distances L1a and L2a from the surface of the substrate 2a to the surface of the film 1 are roughly the same at any positions as shown in FIG. 3A. Thus, the reflection optical path lengths a1a to a3a are equal to one another. Therefore, all of the interference spectra resulting from the reflected light rays h1a to h3a are the same, and hence the film thickness can be determined from the equation (2) with ease.

On the other hand, in the electrophotographic photoreceptor for digital use, the film 1 is formed on the substrate 2b whose surface is rough. The substrate surface is made rougher than that of the one for analog use to prevent the occurrence of interference fringes on the image due to interference between the rays reflected from the surface of the substrate 2b and the rays reflected from the surface of the film 1, of laser light or light from a light-emitting diode. In the photoreceptor, the distances L1b and L2b from the surface of the substrate 2b to the surface of the film 1 are mutually different as shown in FIG. 3B, and the reflection optical path lengths a1b to a3b are also mutually different. Therefore, the interference spectra due to the reflected light rays hib to h3b are mutually different as shown in FIGS. 4A to 4C, and the film thickness is a mean value of the values determined from the equation (2).

In the interference spectra due to the reflected light rays hib to h3b when the substrate 2b is used, shown in FIGS. 4A to 4C, the peak wavelengths of their respective spectra vary according to the reflection optical path lengths a1b to a3b. Actually, since a film region with a constant area is irradiated with light in the light interference method, the interference spectrum obtained is the one of FIG. 4D obtained by combining the spectra of FIGS. 4A to 4C. In the combined spectrum of FIG. 4D, the peaks cancel each other by synthesis of waves, resulting in disappearance of the peaks, on the shorter wavelength side where the distance between peak wavelengths is short. Further, since the distance between peaks is long on the longer wavelength side, the disappearance of the peak due to synthesis of waves hardly occurs. Thus, the disappearance of the peaks tends to occur on the shorter wavelength side, especially at a wavelength of 500 nm or less where the distance between peaks is short.

Further, in the substrate 2b whose surface is relatively rough, light on the shorter wavelength side than the surface roughness Rmax or Rz of the substrate 2b tends to be scattered by the unevenness of the surface of the substrate 2b. However, light on the longer wavelength side than the surface roughness Rmax or Rz of the substrate 2b is less likely to receive the influence of the unevenness of the surface of the substrate 2b, resulting in reduced scattered light. Therefore, use of the light on the longer wavelength side than the surface roughness Rmax or Rz of the substrate 2b causes the interference spectrum to noticeably appear. Thus, it is preferable that film defects are inspected with such light.

In the invention, the inspection of the film defects becomes possible by inspecting the interference spectrum slightly occurring in a photoreceptor for digital use whose substrate has a relatively rough surface. Thus, the photoreceptor which is stable in film thickness and photosensitive characteristics can be manufactured. It is particularly preferable for inspecting such a very weak interference spectrum that the measuring time is elongated, or the dose of light during the measurement is increased until the S/N ratio of the interference spectrum can be sufficiently obtained.

Further, for the photoreceptor so configured that the substrate will completely absorb the irradiation light by applying a light absorption substance on the substrate surface, or imparting the light absorption function to the substrate itself in order to eliminate the light reflected from the substrate, the film defect inspection method of the invention cannot be applied because the interference spectrum cannot be obtained.

Figure 5:
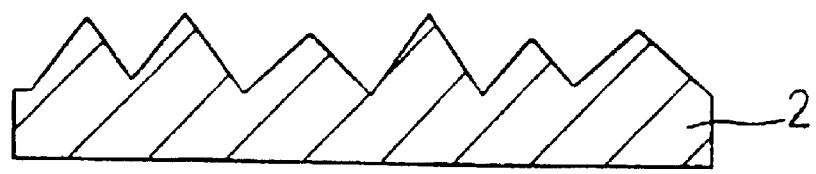
FIG. 5 is a view showing the substrate 2 whose surface has been subjected to a cutting work.
Figure 6:
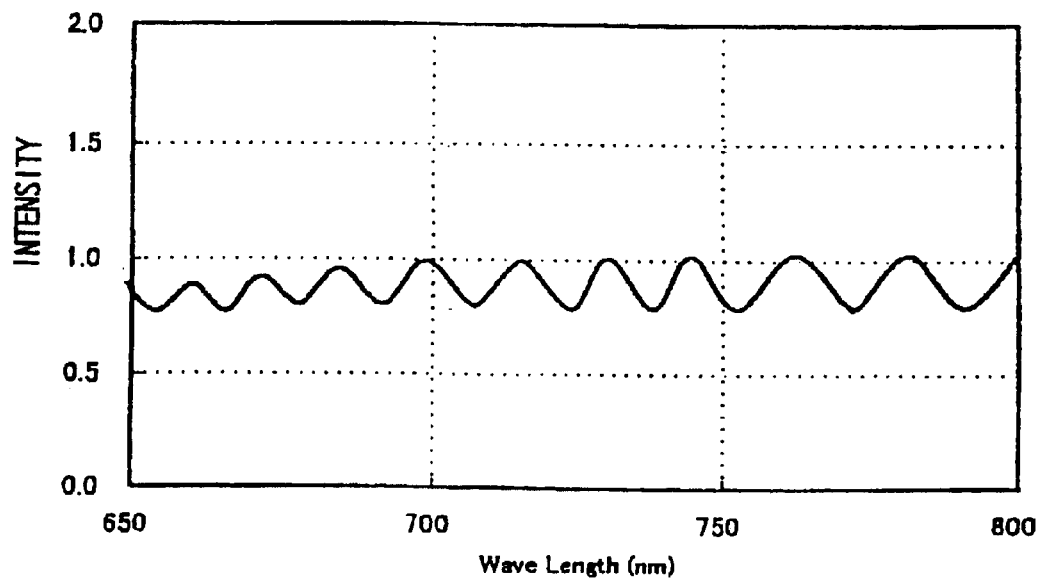
FIG. 6 is a graph showing the interference spectrum of light reflected from the substrate 2.

FIG. 5 is a view showing the substrate 2 whose surface has been subjected to a surface-roughening treatment by a cutting work. Although the surface of the substrate 2 to be used in the photoreceptor for digital use can be subjected to a surface-roughening treatment by various methods, when the surface-roughening treatment is accomplished, for example, by the cutting work, the surface takes the form of repeatedly occurring regular crest and trough. When such a surface of the substrate 2 is irradiated with light, the interference spectrum in the regular wave form of FIG. 6 can be obtained by the light reflected from the substrate 2.

Figure 7A:
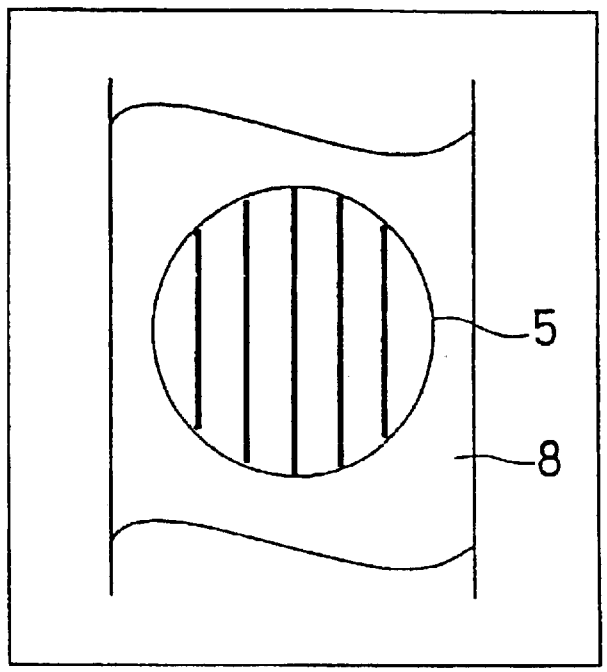
FIG. 7A is a view showing interference fringes 5 when the film thickness uniformity is high.
Figure 7B:
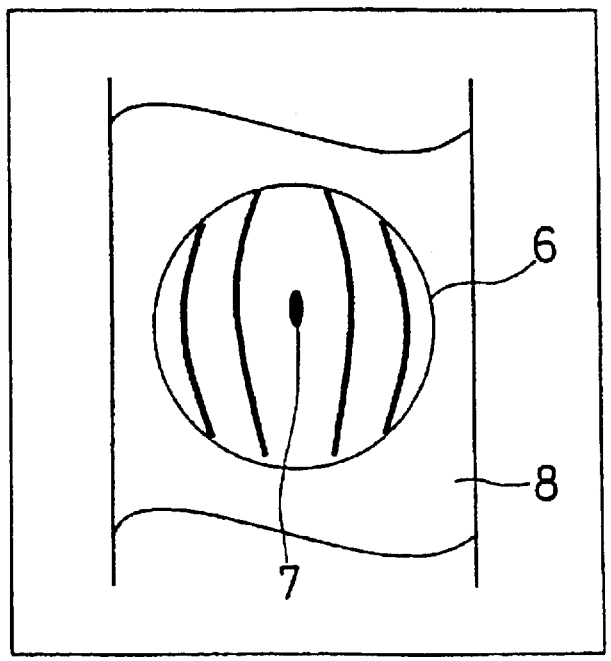
FIG. 7B is a view showing interference fringes 6 when the film thickness uniformity is low.

FIGS. 7A and 7B are views respectively showing the interference fringes 5 and 6 occurring on the film surface of a photoreceptor 8. According to the invention, when the film thickness uniformity is high, the uniform interference fringes 5 of FIG. 7A occur on the film surface by irradiation with the optimized light. On the other hand, when the film thickness uniformity is low, for example, when there occur pinholes 7 due to inclusion of foreign matters, the nonuniform interference fringes 6 of FIG. 7B occur. Such interference fringes 5 and 6 are visually evaluated, and thus the formed films can be classified into good products and defective products depending upon the degree of irregularities of the interference fringes.

FIGS. 8A and 8B are diagrams for illustrating the surface roughnesses Rmax and Rz. The surface roughness is generally expressed as Rmax determined by the maximum difference between the crest and trough of the uneven spot. This surface roughness Rmax is expressed as Ry in accordance with JIS standard B 0601. According to this standard, as shown in FIG. 8A, the roughness curve is extracted along the mean line thereof by the standard length L. The value obtained by measuring the distance between the peak line Rp and the valley line Rv of this extracted portion in the direction of the roughness curve is Rmax. However, when it is expressed as Rmax, it takes a value quite different from the actual value in the case where there occurs a flaw, convex portion, or concave portion within the range to be measured. In particular, the surface roughness of the substrate is generally as small as about 1 $\mu$m. The standard length L in the case of the surface roughness of this order is determined as a relatively short length of 0.8 mm by the standard, and hence the value quite different from the actual value is obtained due to the local flaw, convex portion, or concave portion.

On the other hand, the surface roughness Rz is the parameter for evaluating the surface roughness without receiving the foregoing influence, and the 10-point average value of the surface roughness. In the case where the surface roughness Rz is adopted, the more actual state of the unevenness can be expressed. As shown in FIG. 8B, the surface roughness Rz is the value obtained in the following manner. The roughness curve is extracted along the mean line thereof by the standard length L. Then, the sum of the mean value of the absolute values of the altitudes Yp1 to Yp5 from the highest peak to the fifth peak and the mean value of the absolute values of the altitudes Yv1 to Yv5 from the lowest valley to the fifth valley, measured in the direction of the longitudinal magnification of the mean line of the extracted portion is determined. In the case where the surface roughness or the substrate is expressed as Rz, it is possible to eliminate the influences of the flaw, convex portion, or concave portion within the measuring length when expressed as Rmax.

A description will be given to the example in which the defects or the film formed on the conductive substrate constituting an electrophotographic photoreceptor are inspected according to the defect inspection method of the invention. First, a description will be given to a method for forming the film on the conductive substrate.

Figure 9:
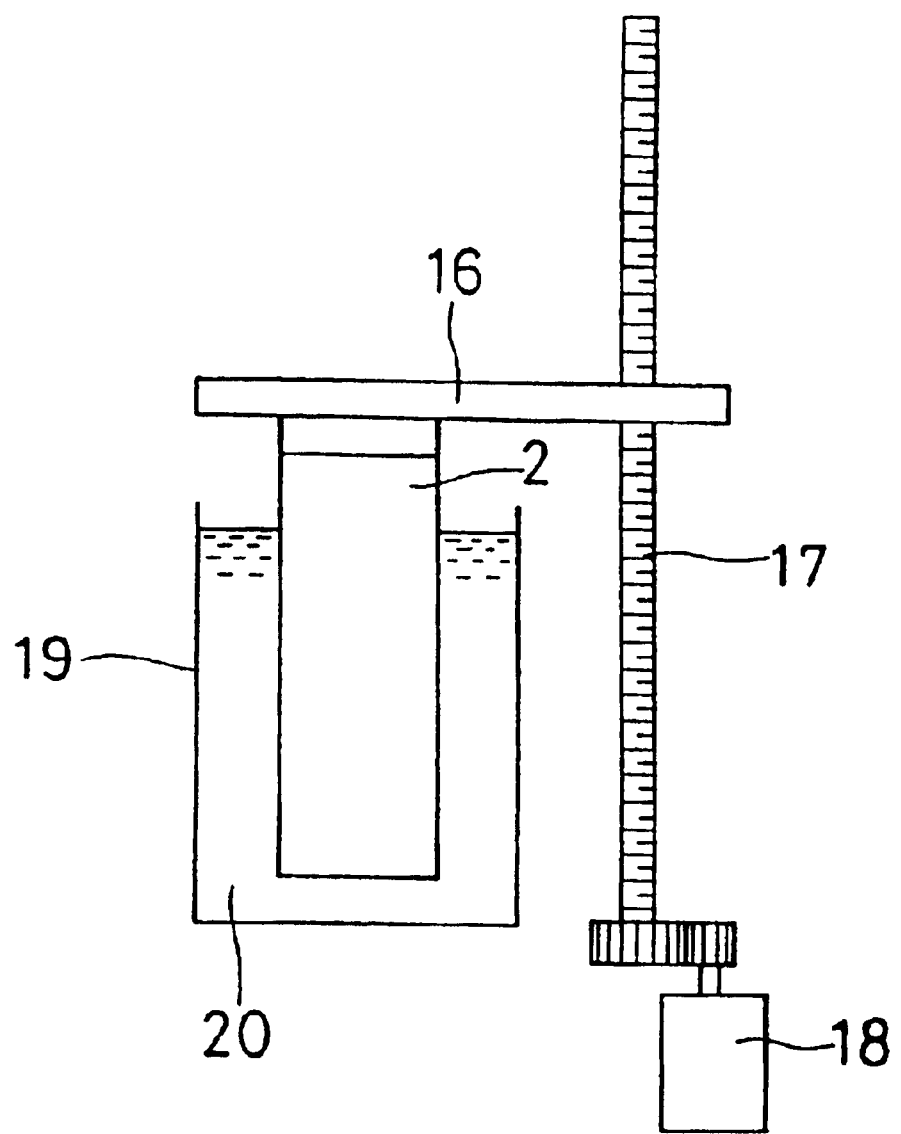
FIG. 9 is a view showing a dip coating apparatus.

FIG. 9 is a view showing a dip coating apparatus. The conductive substrate 2 is fastened to a supporting member 16. The supporting member 16 is coupled to a threaded shaft 17. Thus, an elevating motor 18 is driven to drive the shaft 17 to rotate, causing the up-and-down movement of the supporting member 16. A paint tank 19 in which a paint 20 is contained is placed under the supporting member 16. The supporting member 16 is caused to descend to dip the substrate 2 in the paint 20. Subsequently, the supporting member 16 is caused to ascend to raise the substrate 2. Consequently, the surface of the substrate 2 is coated with the paint 20. In manufacturing a photoreceptor using such a dip coating apparatus, the paints 20 for an undercoat layer, an electric charge generation layer, and an electric charge transport layer are used.

An electrophotographic photoreceptor is so configured that a photosensitive layer is formed on the conductive substrate 2. The photosensitive layer has a laminated structure of the electric charge generation layer and the electric charge transport layer. For example, the electric charge generation layer is formed on the substrate 2, and the electric charge transport layer is formed on the electric charge generation layer. Further, other electrophotographic photosensitive bodies are configured as follows: the undercoat layer is formed on the conductive substrate, and the photosensitive layer having a laminated structure of the electric charge generation layer and the electric charge transport layer is formed on the undercoat layer. For example, the electric charge generation layer is formed on the undercoat layer, and the electric charge transport layer is formed on the electric charge generation layer. The undercoat layer, electric charge generation layer, and electric charge transport layer are formed using the dip coating apparatus. It is noted that the electric charge generation layer and the electric charge transport layer may be laminated in reverse order.

The conductive substrate 2 of the electrophotographic photoreceptor can be implemented by a cylindrical substrate or thin film sheet made of metals such as aluminium, copper, stainless steel, and brass. It can also be implemented by the one obtained by evaporating aluminium, tin, gold, indium oxide, and the like on a cylindrical substrate comprised of a polyester film, paper, and a metal film.

The photoreceptor for digital use, the surface of the substrate 2 is subjected to a surface-roughening treatment. Examples of the method of the surface-roughening treatment include mechanical surface-roughening methods such as cutting method, honing method, etching method, steel ball dropping/impact method, irregularly-shaped cylindrical body pressure welding method, grinding method, laser irradiation method, and high-pressure water injection method; and chemical surface-roughening method such as anodic oxidation method, boehmite treatment method, and heating oxidation treatment method.

The undercoat layer is provided on the substrate 2 for improving the adhesive property and coating property of the photosensitive layer, or for improving the coating of the defects on the substrate 2 and the electric charge-injection property from the substrate 2 to the electric charge generation layer. Materials used for the undercoat layer, include resins such as polyamide, copolymer nylon, casein, polyvinyl alcohol, cellulose, and gelatin. These resins are dissolved in an organic solvent to prepare a paint Then, the resulting paint is applied onto the substrate 2 so that the film thickness is about 0.1 μm to 5 μm using the dip coating apparatus. Further, in order to improve the electrophotographic characteristics, for example, under the low-temperature and low-humidity environment, and adjust the resistivity of the undercoat layer, inorganic pigments such as alumina, tin oxide, and titanium oxide may be dispersed in the undercoat layer, if required.

The electric charge generation layer contains an electric charge generation material for generating electric charges by irradiation with light as a main component. It may also contain known binders, plasticizers, and sensitizers, if required. Examples of the electric charge generation material include perylene-based pigments, polycyclic quinone-based pigments, metal-free phthalocyanine pigments, metal phthalocyanine pigments, squarylium dye, azulenium dye, thiapyrylium dye, and azo pigments having a carbazole skeleton, styryl stilbene skeleton, triphenylamine skeleton, didenzothiophene skeleton, oxadiazole skeleton, fluorenone skeletone, bisstilbene skeleton, distyryloxadiazole skeleton, and distyrylcarbazole skeleton. As the photoreceptor for digital use, in particular, metal-free phthalocyanine pigments, metal phthalocyanine pigments, and azo pigments are preferable.

The electric charge transport layer contains an electric charge transport material for receiving the electric charges generated by the electric charge generation material, and transporting them, and a binder as essential components. It may also contain known plasticizers, sensitizers, and silicone-based levelling agents, if required. Examples of the electric charge transport material include electron-donating substances such as poly-N-vinylcarbazole and derivatives thereof, poly-γ-carbazolyl ethyl glutamate and derivatives thereof, pyrene-formaldehyde condensate and derivatives thereof, polyvinylpyrene, polyvinylphenanthrene, oxazole derivatives, oxodiazole derivatives, imidazole derivatives, 9-(p-diethylaminostyryl)anthracene, 1,1-bis(4-dibenzyl-aminophenyl)propane, styryl anthracene, styryl pyrazoline, phenylhydrazones, and hydrazone derivatives. Further, there can be mentioned electron-receiving substances such as fluorenone derivatives, dibenzothiophene derivatives, indenothiophene derivatives, phenanthrenequinone derivatives, indenopyridine derivatives, thioxanthone derivatives, benzo[c]cinnoline derivatives, phenazine oxide derivatives, tetracyanoethylene, tetracyanoquinodimethane, bromanil, chloranil, and benzoin.

As the binders for the electric charge transport layer, the ones having compatibility with the electric charge transport materials are selected. Examples thereof include polycarbonate, polyvinyl butyral, polyamide, polyester, polyketone, epoxy resins, polyurethane, polyvinyl ketone, polystyrene, polyacrylamide, phenol resins, and phenoxy resins.

Next, a description will be given to one example of the manufacturing method of the electrophotographic photoreceptor. Titanium oxide and copolymer nylon resin are dispersed in adequate solvents such as ethanol, methanol, and a mixed solvent of methanol and dichloroethane to prepare a paint for the undercoat layer. Then, the conductive substrate 2 is dipped in the paint using the dip coating apparatus, raised, and dried to form the undercoat layer on the substrate 2.

The electric charge generation materials such as azo pigments are dispersed in adequate solvents such as cyclohexanone, benzene, chloroform, dichloroethane, ethyl ether, acetone,ethanol, chlorobenzene, and methyl ethyl ketone, if required, with binders, plasticizers, and sensitizers to prepare a paint for the electric charge generation layer. Then, the conductive substrate 2 or the conductive substrate on which the undercoat layer is formed is dipped in the paint using the dip coating apparatus, raised, and dried to form the electric charge generation layer on the substrate 2 or the undercoat layer.

The electric charge transport materials such as hydrazone-based compounds, silicon-based levelling agents, and binders are dispersed in adequate solvents such as dichloroethane, benzene, chloroform, cyclohexanone, ethyl ether, acetone, ethanol, chlorobenzene, and methyl ethyl ketone, if required, with plasticizers, and sensitizers to prepare a paint for the electric charge transport layer. Then, the conductive substrate 2 on which the electric charge generation layer is formed is dipped in the paint using the dip coating apparatus, raised, and dried to form the electric charge transport layer on the electric charge generation layer.

EXAMPLE 1

One part by weight of phthalocyanine pigment, 1 part by weight of butyral resin (Eslec BM-2, manufactured by Sekisui Chemical Co., Ltd.), and 120 parts by weight of cyclohexanone were mixed, and dispersed by a ball mill for 12 hours, thus preparing a paint for the electric charge generation layer. On the other hand, there was prepared the conductive substrate 2 which was a cylindrical substrate made of aluminium, and had a surface subjected to a cutting work, respective surface roughnesses Rmax of 0.50 $\mu$m, 0.60 $\mu$m, and 0.65 $\mu$m, an outer diameter $\phi$ of 65 mm, and a length of 330 mm. Then, the paint for the electric charge generation layer was used to be applied thereon using the dip coating apparatus of FIG. 9 so that the film thickness was about 0.5 $\mu$m, thereby forming the electric charge generation layer on the substrate 2.

Next, 1 part by weight of hydrazone-based electric charge transport material (ABPH, manufactured by Nippon Kayaku Co., Ltd.), 1 part by weight of polycarbonate (PANLIGHT L-1250, manufactured by Teijin Kasei Co., Ltd.), 0.00013 part by weight of silicone-based levelling agent(KF-96, manufactured by The Shin-Etsu Chemical Co., Ltd.) were added to 8 parts by weight of dichloroethane, heated at 45° C., and completely dissolved. Thereafter, the solution was air-cooled to prepare a paint for the electric charge transport layer. The paint was applied using the dip coating apparatus of FIG. 9 so that the film thickness was about 20 $\mu$m, thereby forming the electric charge transport layer on the electric charge generation layer. Thus, photosensitive bodies were manufactured.

For the 3 kinds of photosensitive bodies manufactured, the wavelength of light to be applied thereto for the defect inspection is set in the range of 350 to 450 nm, 400 nm to 500 nm, 450 nm to 550 nm, 500 nm to 600 nm, 550 nm to 650 nm, 600 nm to 700 nm, and 650 nm to 750 nm. Thus, the photosensitive bodies were evaluated for the occurrence of the interference fringes on the film surface upon irradiation with these rays of light. The results are shown in Table 2. In Table 2, "○" indicates that the interference fringes occurred, and the visual evaluation of the coating nonuniformity was possible. Whereas "X" indicates that the interference fringes did not occur, and the visual evaluation of the coating nonuniformity was impossible.

TABLE 2

| Irradiation wavelength range (nm) | Rmax 0.50 ($\mu$m) | Rmax 0.60 ($\mu$m) | Rmax 0.65 ($\mu$m) |
| --- | --- | --- | --- |
| 350–450 | x | x | x |
| 400–500 | x | x | x |
| 450–550 | x | x | x |
| 500–600 | ○ | x | x |
| 550–650 | ○ | x | x |
| 600–700 | ○ | ○ | x |
| 650–750 | ○ | ○ | ○ |

As indicated from Table 2, irradiation with light of a wavelength larger than the surface roughness Rmax of the substrate causes the interference fringes to occur on the photoreceptor surface, and hence it is possible to inspect the defects of the film on the substrate. It is also indicated that, especially when the substrate with a surface roughness Rmax of 0.5 $\mu$m or more is used, the interference fringes occur on the photoreceptor surface by irradiation with light of a wavelength of 500 nm or more, and hence it is possible to inspect the defects of the film on the substrate.

Then, each photoreceptor using the substrate with a surface roughness Rmax of 0.60 $\mu$m was irradiated with light of a wavelength in the range of 650 nm to 750 nm to generate the interference fringes. Then, the coating nonuniformity was classified into 3 ranks of A, B, and C by visual observation along the length thereof. Further, 10 photosensitive bodies of each rank were mounted in a digital copier (AR-330, manufactured by Sharp Corp.), and determined for their respective surface potentials along the length thereof when charged at −600 V. Then, the maximum values, minimum values, and variations (standard deviations σ) were evaluated. The results are shown in Table 3. In Table 3, the visually evaluated rank A denotes the one judged as being free from coating nonuniformity by visual inspection. The visually evaluated rank B denotes the one judged as exhibiting slight coating nonuniformity. The visually evaluated rank C denotes the one judged as being defective because of bad coating nonuniformity.

TABLE 3

| | Maximum Value (V) | Minimum value (V) | Standard deviation (σ) |
| --- | --- | --- | --- |
| Visually evaluated rank A | −602 | −599 | 1.16 |
| Visually evaluated rank B | −608 | −591 | 6.15 |
| Visually evaluated rank C | −620 | −580 | 12.66 |

Table 3 reveals that there is the correlation between the results of the visual inspection and the results of variations in surface potential. Thus, it is indicated that the results of the visual inspection has a high degree of accuracy. Further, the same results were also obtained for the photosensitive bodies using substrates with other surface roughnesses.

EXAMPLE 2

There was prepared the conductive substrate 2 which was a cylindrical substrate made of aluminium, and had a surface subjected to a cutting work, a surface roughness Rmax of 0.50 $\mu$m, and an outer diameter $\phi$ of 65 mm. Thus, the electric charge generation layer and electric charge transport layer were formed in the same manner as in Example 1 to manufacture photosensitive bodies.

The photosensitive bodies thus manufactured were respectively irradiated with 580-nm monochromatic light, and 550- to 650-nm light, for the defect inspection. Thus, the interference fringes occurred on the film surface of each photoreceptor were visually evaluated to measure the number of foreign matters. The photosensitive bodies were also mounted in the same copier as that of Example 1 to form half-tone images. Then, each image quality was inspected to measure the number of black points and white points each with a diameter of 1 mm or more on the image as the defects. These results are shown in Table 4. In Table 4, the visually inspected result A denotes the number of foreign matters when 580-nm monochromatic light was used. The visually inspected result B denotes the number of foreign matters when 550- to 650-nm light was used. The image check result denotes the number of defects (black points and white points) found on the image.

TABLE 4

|  | Visually inspected result A | Visually inspected result B | Image check result |
|---|---|---|---|
| Photoreceptor 1 | 8 | 4 | 8 |
| Photoreceptor 2 | 7 | 2 | 6 |
| Photoreceptor 3 | 2 | 1 | 2 |
| Photoreceptor 4 | 4 | 0 | 4 |
| Photoreceptor 5 | 0 | 0 | 0 |
| Photoreceptor 6 | 17 | 7 | 18 |
| Photoreceptor 7 | 5 | 2 | 5 |
| Photoreceptor 8 | 9 | 3 | 8 |
| Photoreceptor 9 | 11 | 5 | 9 |
| Photoreceptor 10 | 6 | 3 | 7 |

Figure 10:
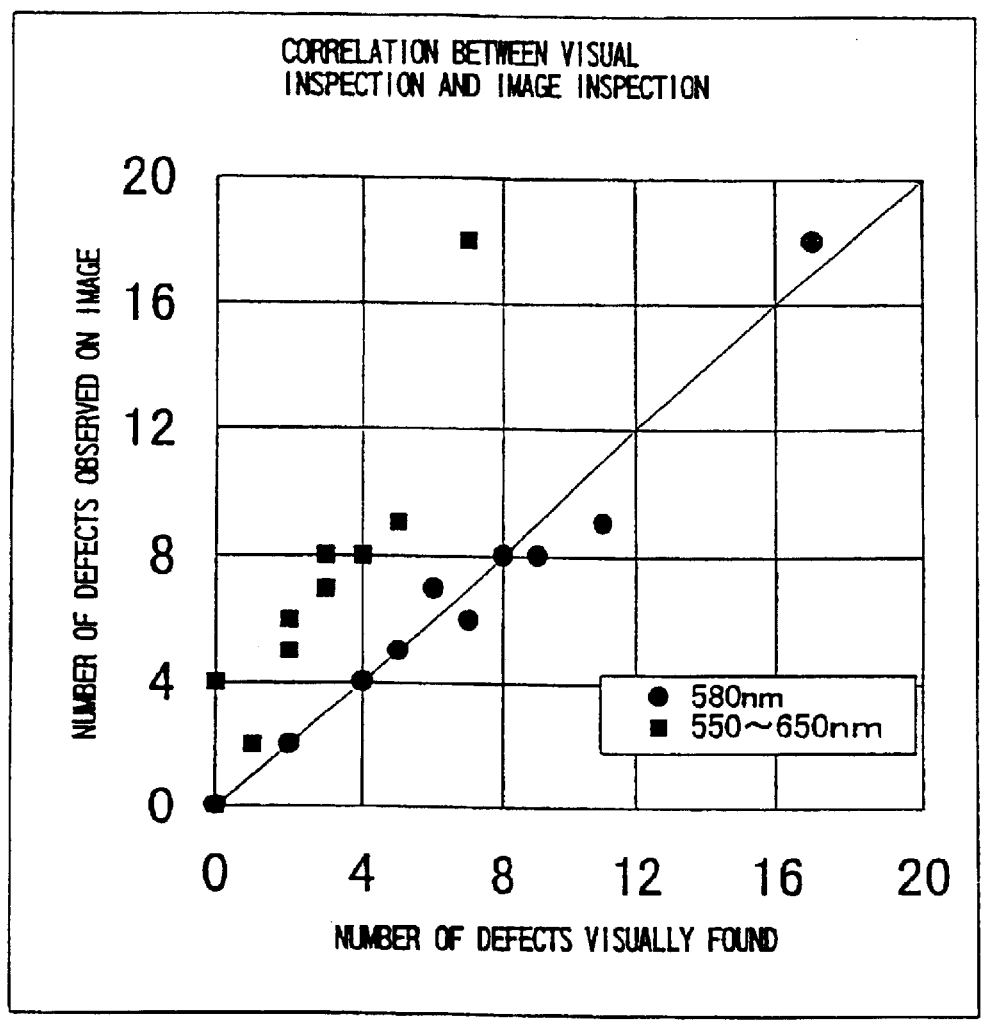
FIG. 10 is a graph showing the relationship between the number of foreign matters by visual inspection and the number of defects found on the image.

FIG. 10 is a graph showing the relationship between the number of foreign matters by visual inspection and the number of defects found on the image. Table 4 indicates that the interference fringes occur from both of the light rays, and hence the inspection of the defects is possible. However, the graph of FIG. 10 indicates that the visual inspection results for 580-nm monochromatic light show a higher percentage of finding the defects than with the visual inspection results for 550- to 650-nm light. Therefore, it is indicated that use of monochromatic light enables the defect inspection with a high accuracy.

EXAMPLE 3

Figure 11:
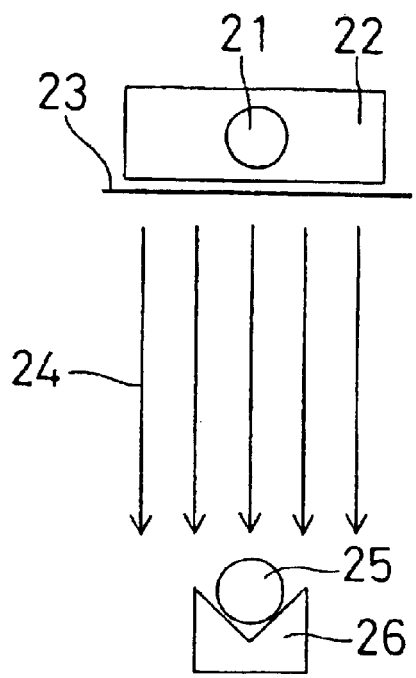
FIG. 11 is a view showing an irradiation method of indirect light 24.
Figure 12:
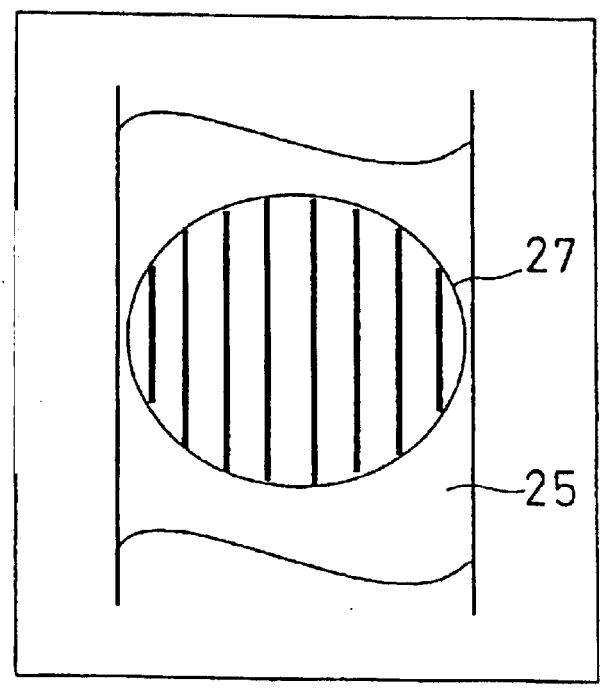
FIG. 12 is a view showing interference fringes 27 obtained when film defects are inspected by irradiation with indirect light 24.

The photoreceptor manufactured in Example 2 was inspected for the film defects by irradiation with indirect light. FIG. 11 is a view showing the irradiation method of indirect light 24. Further, FIG. 12 is a view showing the interference fringes obtained in this step. The indirect light 24 is obtained by allowing light from a light source 21 to pass through a reflector plate 22 and a diffusing plate 23. An electrophotographic photoreceptor 25 is mounted on a supporting mount 26, and this photoreceptor 25 is irradiated with the indirect light 24.

Comparative Example 1

Figure 13:
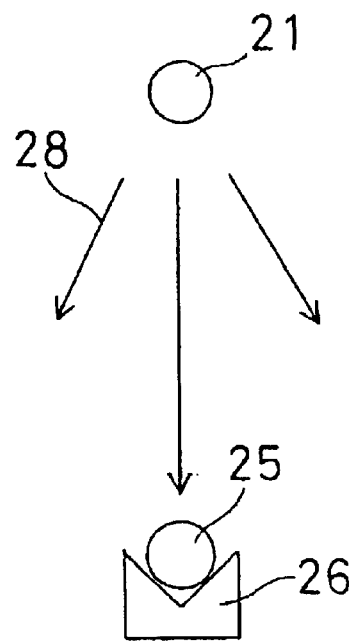
FIG. 13 is a view showing an irradiation method of direct light 28.
Figure 14:
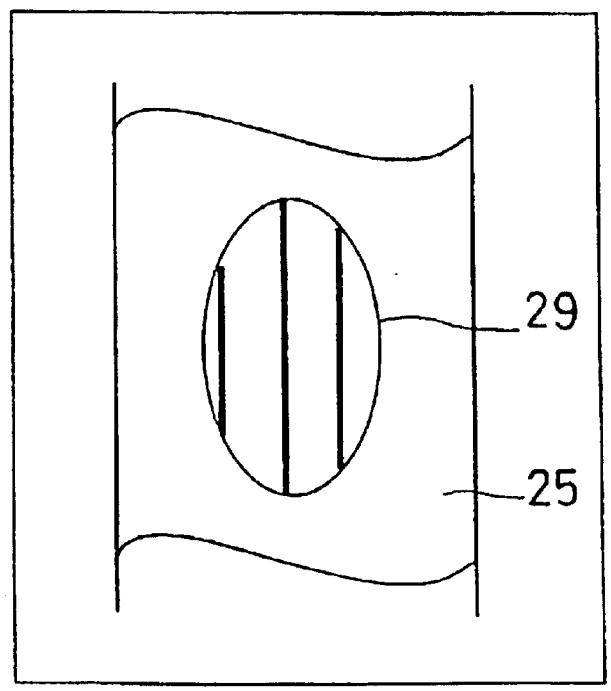
FIG. 14 is a view showing interference fringes 29 obtained when film defects are inspected by irradiation with direct light 28.

The photoreceptor manufactured in Example 2 was inspected for the film defects by irradiation with direct light 28. FIG. 13 is a view showing the irradiation method of the direct light 28. Further, FIG. 14 is a view showing the interference fringes 29 obtained at this step. The direct light 28 is the light emitted directly from the light source 21.

It is indicated that the interference fringes 27 can be obtained in a wider range in Example 3 as compared with Comparative Example 1. In Example 3, the inspection time of the defects per photoreceptor was found to be about 30 seconds. In contrast, the interference fringes 29 could be obtained only in a narrow range in Comparative Example 1. The inspection time of the defects per photoreceptor was found to be about 2 minutes and 30 seconds.

EXAMPLE 4

One part by weight of phthalocyanine pigment, 1 part by weight of butyral resin (Eslec BM-2, manufactured by Sekisui Chemical Co., Ltd.), and 120 parts by weight of cyclohexanone were mixed, and dispersed by a ball mill for 12 hours, thus preparing a paint for the electric charge generation layer. On the other hand, there was prepared the conductive substrate 2 which was a cylindrical substrate made of aluminium, and had a surface subjected to a cutting work, respective surface roughnesses Rz of 0.50 μm, 0.60 μm, and 0.65 μm, an outer diameter φ of 65 mm, and a length of 330 mm. Then, the paint for the electric charge generation layer was used to be applied thereon using the dip coating apparatus of FIG. 9 so that the film thickness was about 0.5 μm, thereby forming the electric charge generation layer on the substrate 2.

Next, 1 part by weight of hydrazone-based electric charge transport material (ABPH, manufactured by Nippon Kayaku Co., Ltd.), 1 part by weight of polycarbonate (PANLIGHT L-1250, manufactured by Teijin Kasei Co., Ltd.), 0.00013 part by weight of silicone-based levelling agent(KF-96, manufactured by Shin-Etsu Chemical Co., Ltd.) were added to 8 parts by weight of dichloroethane, heated at 45° C., and completely dissolved. Thereafter, the solution was air-cooled to prepare a paint for the electric charge transport layer. The paint was applied using the dip coating apparatus of FIG. 9 so that the film thickness was about 20 μm, thereby forming the electric charge transport layer on the electric charge generation layer. Thus, photosensitive bodies were manufactured.

For the 3 kinds of photosensitive bodies manufactured, the wavelength of light to be applied thereto for the defect inspection is set in the range of 350 to 450 nm, 400 nm to 500 nm, 450 nm to 550 nm, 500 nm to 600 nm, 550 nm to 650 nm, 600 nm to 700 nm, and 650 nm to 750 nm. Thus, the photosensitive bodies were evaluated for the occurrence of the interference fringes on the film surface upon irradiation with these rays of light. The results are shown in Table 5. In Table 5, "○" indicates that the interference fringes occurred, and the visual evaluation of the coating nonuniformity was possible. Whereas "X" indicates that the interference fringes did not occur, and the visual evaluation of the coating nonuniformity was impossible.

TABLE 5

| Irradiation wavelength range (nm) | Rz 0.50 | Rz 0.60 | Rz 0.65 |
|---|---|---|---|
| 350–450 | x | x | x |
| 400–500 | x | x | x |
| 450–550 | x | x | x |
| 500–600 | ○ | x | x |
| 550–650 | ○ | x | x |
| 600–700 | ○ | ○ | x |
| 650–750 | ○ | ○ | ○ |

As indicated from Table 5, irradiation with light of a wavelength larger than the surface roughness Rz of the substrate 2 causes the interference fringes to occur on the photoreceptor surface, and hence it is possible to inspect the defects on the substrate surface. It is also indicated that, especially when the substrate 2 with a surface roughness Rz of 0.5 μm or more is used, the interference fringes occur on the photoreceptor surface by irradiation with light of a wavelength of 500 nm or more, and hence it is possible to inspect the defects of the film on the substrate.

Then, each photoreceptor using the substrate 2 with a surface roughness Rz of 0.60 μm was irradiated with light of a wavelength in the range of 650 nm to 750 nm to generate the interference fringes. Then, the coating nonuniformity was classified into 3 ranks of A, B, and C by visual observation along the length thereof. Further, 10 photosensitive bodies of each rank were mounted in a digital copier (AR-330, manufactured by Sharp Corp.), and determined for their respective surface potentials along the length thereof when charged at −600 V. Then, the maximum values, minimum values, and variations (standard deviations σ) were evaluated. The results are shown in Table 6. In Table 6, the visually evaluated rank A denotes the one judged as being free from coating nonuniformity by visual inspection. The visually evaluated rank B denotes the one judged as exhibiting slight coating nonuniformity. The visually evaluated rank C denotes the one judged as being defective because of bad coating nonuniformity.

TABLE 6

|  | Maximum Value (V) | Minimum value (V) | Standard deviation (σ) |
| --- | --- | --- | --- |
| Visually evaluated rank A | −601 | −598 | 1.12 |
| Visually evaluated rank B | −607 | −589 | 6.37 |
| Visually evaluated rank C | −622 | −581 | 13.08 |

Table 6 reveals that there is the correlation between the results of the visual inspection and the results of variations in surface potential. Thus, it is indicated that the results of the visual inspection has a high degree of accuracy. Further, the same results were also obtained for the photosensitive bodies using substrates with other surface roughnesses.

EXAMPLE 5

There was prepared the conductive substrate 2 which was a cylindrical substrate made of aluminium, and had a surface subjected to a cutting work, a surface roughness Rz of 0.60 μm, and an outer diameter φ of 65 mm. Thus, the electric charge generation layer and electric charge transport layer were formed in the same manner as in Example 4 to manufacture photosensitive bodies.

The photosensitive bodies thus manufactured were respectively irradiated with 620-nm monochromatic light, and 600- to 700-nm light, for the defect inspection. Thus, the interference fringes occurred on the film surface of each photoreceptor were visually evaluated to measure the number of foreign matters. The photosensitive bodies were also mounted in the same copier as that of Example 4 to form half-tone images. Then, each image quality was inspected to measure the number of black points and white points each with a diameter of 1 mm or more on the image as the defects. These results are shown in Table 7. In Table 7, the visually inspected result A denotes the number of foreign matters when 620-nm monochromatic light was used. The visually inspected result B denotes the number of foreign matters when 600- to 700-nm light was used. The image check result denotes the number of defects (black points and white points) found on the image.

TABLE 7

|  | Visually inspected result A | Visually inspected result B | Image check result |
| --- | --- | --- | --- |
| Photoreceptor 1 | 12 | 4 | 13 |
| Photoreceptor 2 | 4 | 1 | 5 |
| Photoreceptor 3 | 8 | 1 | 8 |
| Photoreceptor 4 | 16 | 4 | 14 |
| Photoreceptor 5 | 2 | 0 | 2 |
| Photoreceptor 6 | 23 | 12 | 25 |
| Photoreceptor 7 | 6 | 3 | 5 |

TABLE 7-continued

|  | Visually inspected result A | Visually inspected result B | Image check result |
| --- | --- | --- | --- |
| Photoreceptor 8 | 7 | 2 | 8 |
| Photoreceptor 9 | 10 | 2 | 9 |
| Photoreceptor 10 | 7 | 1 | 7 |

Figure 15:
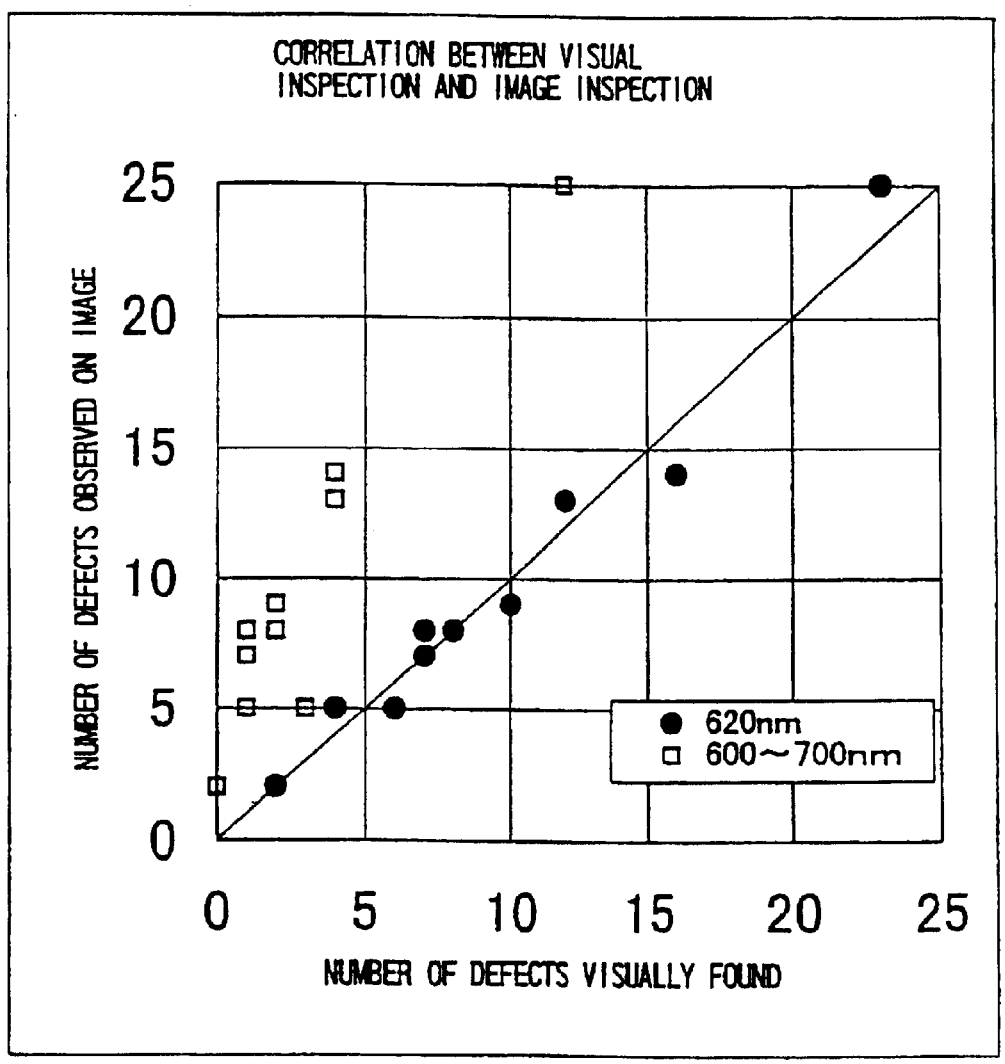
FIG. 15 is a graph showing the relationship between the number of foreign matters by visual inspection and the number of defects found on the image.

FIG. 15 is a graph showing the relationship between the number of foreign matters by visual inspection and the number of defects found on the image. Table 7 indicates that the interference fringes occur from both of the light rays, and hence the inspection of the defects is possible. However, the graph of FIG. 15 indicates that the visual inspection results for 620-nm monochromatic light show a higher percentage of finding the defects than with the visual inspection results for 600- to 700-nm light. Therefore, it is indicated that use of monochromatic light enables the defect inspection with a high accuracy.

EXAMPLE 6

The photoreceptor manufactured in Example 5 was inspected for the film defects by irradiation with indirect light. As shown in FIG. 11, the indirect light 24 is obtained by allowing light from the light source 21 to pass through the reflector plate 22 and the diffusing plate 23. The electrophotographic photoreceptor 25 is mounted on the supporting mount 26, and this photoreceptor 25 is irradiated with the indirect light 24. In this step, the interference fringes 27 of FIG. 12 were obtained.

Comparative Example 2

The photoreceptor manufactured in Example 5 was inspected for the film defects by irradiation with direct light 28. The direct light 28 is the light emitted directly from the light source 21 as shown in FIG. 13. In this step, the interference fringes 29 of FIG. 14 were obtained.

It is indicated that the interference fringes 27 can be obtained in a wider range in Example 6 as compared with Comparative Example 2. In Example 6, the inspection time of the defects per photoreceptor was found to be about 30 seconds. In contrast, the interference fringes 29 could be obtained only in a narrow range in Comparative Example 2. The inspection time of the defects per photoreceptor was found to be about 2 minutes and 30 seconds.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A film defect inspection method for inspecting defects of a film formed on a substrate by a light interference method, comprising:
   irradiating the substrate with light of a longer wavelength than a surface roughness Rmax of the substrate; and
   inspecting interference fringes occurring on the film surface in response to the irradiated light for detecting defects in the film, said defects consisting of inclusion of foreign matter in the film and occurrences of variations in the film thickness.

2. The film defect inspection method of claim 1, wherein the substrate is irradiated with light of a wavelength of more than 500 nm when the surface roughness Rmax of the substrate is 0.5 μm.

3. The film defect inspection method of claim 1, wherein the substrate surface is subjected to a cutting work.

4. The film defect inspection method of claim 1, wherein the substrate is electrically conductive, and on the substrate are formed an electric charge generation layer, and an electric charge transport layer or an undercoat layer, which constitute an electrophotographic photoreceptor along with the substrate.

5. The film defect inspection method of claim 4, wherein the electrophotographic photoreceptor is one for digital copiers or printers.

6. The film defect inspection method of claim 14, wherein the electrophotographic photoreceptor is one for digital copiers or printers.

7. The film defect inspection method of claim 1, wherein the substrate is irradiated with monochromatic light or indirect light, and the indirect light is light reflected from a reflector plate or light diffused by a diffusion plate.

8. The film defect inspection method of claim 1, wherein the film defect inspection is an inspection of variations in film thickness or an inspection of foreign matters in the film.

9. The film defect inspection method of claim 1, wherein the substrate is irradiated with light of a wavelength of more than 600 nm, when the surface roughness Rmax of the substrate is 0.6 μm.

10. The film defect inspection method of claim 1, wherein the substrate is irradiated with light of a wavelength of more than 650 nm, when the surface roughness Rmax of the substrate is 0.65 μm.

11. A film defect inspection method for inspecting defects of a film formed on a substrate by a light interference method, comprising:

irradiating the substrate with light of a longer wavelength than a surface roughness Rz of the substrate; and inspecting interference fringes occurring on the film surface in response to the irradiated light for detecting defects in the film, said defects consisting of inclusion of foreign matter in the film and occurrences of variations in the film thickness.

12. The film defect inspection method of claim 11, wherein, when the surface roughness Rz of the substrate is 0.5 μm, the substrate is irradiated with light of a wavelength of more than 500 nm.

13. The film defect inspection method of claim 11, wherein the substrate surface is subjected to a cutting work.

14. The film defect inspection method of claim 11, wherein the substrate is electrically conductive, and on the substrate are formed an electric charge generation layer, and an electric charge transport layer or an undercoat layer, which constitute an electrophotographic photoreceptor along with the substrate.

15. The film defect inspection method of claim 11, wherein the substrate is irradiated with monochromatic light or indirect light, and the indirect light is light reflected from a reflector plate or light diffused by a diffusion plate.

16. The film defect inspection method of claim 11, wherein the film defect inspection is an inspection of variations in film thickness or an inspection of foreign matters in the film.

17. The film defect inspection method of claim 11, wherein the substrate is irradiated with light of a wavelength of more than 600 nm, when the surface roughness Rz of the substrate is 0.6 μm.

18. The film defect inspection method of claim 11, wherein the substrate is irradiated with light of a wavelength of more than 650 nm, when the surface roughness Rz of the substrate is 0.65 μm.

* * * * *